US00PP09082P

United States Patent [19]

Button et al.

[11] Patent Number: Plant 9,082

[45] Date of Patent: Mar. 14, 1995

[54] AGLAONEMA PLANT NAMED 'SILVER FROST'

[75] Inventors: Richard J. Button, Miami; Ann E. Lamb, Lake Placid, both of Fla.

[73] Assignee: Sunshine Foliage World, Zolfo Springs, Fla.

[21] Appl. No.: 223,997

[22] Filed: Apr. 6, 1994

[51] Int. Cl.[6] ..... A01H 5/00

[52] U.S. Cl. ..... Plt./88.1

[58] Field of Search ..... Plt. 88.1

*Primary Examiner*—Howard J. Locker

*Attorney, Agent, or Firm*—Foley & Lardner

[57] ABSTRACT

An Aglaonema plant named Silver Frost characterized by its silver-green leaves marked in the center and along the margin with dark green; tall, upright, spreading habit; rapid growth; and noticeable tolerance to cold.

2 Drawing Sheets

The present invention comprises a new and distinct cultivar of Aglaonema, botanically known as *Aglaonema hybrida*, and referred to by the cultivar name Silver Frost. The new cultivar is a product of a planned breeding program carried out by the inventor Richard J. Button in Miami, Fla. The new cultivar was selected from the progeny of a cross made by the inventor between Aglaonema Emerald Beauty (female parent) and Aglaonema Silver Queen (male parent).

The first act of asexual propagation of Silver Frost occurred when offshoots and tissue culture of plants of the new cultivar were taken in Palmdale, Fla., under the supervision of inventor Ann E. Lamb. That and subsequent asexual reproduction both by tissue culture and offshoots have clearly established that the combination of characteristics of the new cultivar disclosed herein are firmly fixed and are retained through successive generations of asexual reproduction.

The following observations, measurements and values describe plants grown in Zolfo Springs, Fla., under shade house conditions which closely approximate those generally used in horticulture practice.

The following traits have been repeatedly observed to be characteristics which in combination distinguish Silver Frost from other Aglaonema of the same general type, for example, the well-known cultivar Silver Queen, to which Silver Frost is compared.

1. The leaves of Silver Frost are larger, and wider and are almost completely overlaid with silver-green markings.

2. The leaves of Silver Frost have dark green markings radiating out from the midrib and speckles along the leaf margin.

3. The habit of Silver Frost is taller, more upright, and spreading when compared to Silver Queen.

4. Plants of Silver Frost grown to a marketable size in approximately 20% less time than Silver Queen.

5. Plants of Silver Frost, unlike Silver Queen, display little or no foliar damage when exposed to 40° F. for approximately 3 hours.

All color references are measured against the Royal Horticultural Society Colour Chart. Colors are approximate as color depends on horticulture practices such as light level and fertilization rate, among others, without, however, any variance in genotype.

The drawings comprise a color photograph and color photocopy.

The color photograph on sheet 1 comprises a perspective view of a plant of Silver Frost in a 26 cm pot approximately 69 weeks after planting a single four-leaf cutting and grown under appropriate growing conditions.

The color photocopy on sheet 2 shows in greater detail the leaf color pattern on the adaxial surface. Colors are as accurate as possible with color illustrations of this type.

Origin: Seedling selected from a cross of Aglaonema Emerald Beauty × Aglaonema Silver Queen.

Classification: Aglaonema hybrida, cv Silver Frost.

Propagation: Asexual propagation either by division or tissue culture.

Plant: When a four-leaf cutting is grown in a 26 cm pot for approximately 69 weeks under appropriate growing conditions, mature plants of Silver Frost are approximately 24.0 to 26.5 cm. in height measured from the soil surface to the junction of the petioles of the last two (2) unrolled leaves, and approximately 85 cm to 92 cm in width.

Stem:

*Growth pattern.*—The stem is erect in growth and approximately 1.7 cm to 1.9 cm in diameter five (5) cm above the soil surface. Internode distance is approximately 0.7 cm to 1.2 cm three (3) cm above the soil.

*Color.*—Immature: 145 A–B; Mature: 152 C–D.

Petiole: The following information is based on the fourth expanded leaf from the apex.

*Growth pattern.*—The petiole has fleshy edges extending from the midrib and referred to as wings. The wings are approximately 4 mm to 6 mm wide one-half the distance from the petiole base to the wing apex. The wings extend from the base of the petiole to within approximately 3.5 cm of the base of the leaf. The apex of the wings is unevenly rounded and often torn. The petiole follows the stem axis but diverges from the axis approximately 5.8 cm to 6.7 cm from the leaf base, forming a horizontal distance from the edge of the stem to the leaf base of approximately 3.5 cm to 4.2 cm.

*Dimensions.*—The petiole is straight from its base to approximately the end of the wing, and often curved from approximately the end of the wing to the base of the leaf. The petiole is approximately 7 mm to 9 mm in diameter one-half the distance between the top of the wing and the base of the leaf. The petiole is approximately 19.0 cm to 20.0 cm in length.

*Color.*—The petiole color is 146 B–C lightly mottled with 146 D. The petiole wings are 146 B lightly mottled with 146 D.

Leaf:

*Growth pattern.*—The leaf is ovate with an acuminate apex and an obtuse base. The margin is entire. The leaf is asymmetric with the side of the leaf unrolling first having less surface area than the side unrolling last. The leaf is oriented parallel to the stem axis at the time of full unrolling, changing to approximately 50 degrees above perpendicular to the stem axis as more leaves unroll above it. The midrib is straight and the leaf tip is curved downward. The leaf blade is flat from the midrib to the margin. The leaf blades often fold upward from the midrib at approximately 45 degrees.

*Dimensions.*—For the pot size and growing time indicated, the largest leaves are approximately 33.0 cm to 36.0 cm long and approximately 11.5 cm to 13.3 cm wide. Average sized leaves are approximately 26.0 cm to 28.5 cm long and approximately 9.2 cm to 10.9 cm wide. The leaf is moderately thick.

*Midrib.*—The midrib is thick and prominent, recessed on the adaxial leaf surface and protruding from the abaxial surface. When new, the color of the adaxial leaf midrib is predominately 137 A–B, lightening to 138 C–D on the lower one-third of the midrib. The color of the adaxial midrib of the mature leaf is predominately greener than, but closest to, 139 A, lightening to 138 A–B on the lower one-third of the midrib. The abaxial midrib is 146 B–C, lightly mottled with 146 D on both new and old leaves.

*Primary veins.*—The primary veins are sunken into the upper surface and protrude slightly from the underside. The primary veins are the same color as the surrounding leaf tissue on both leaf surfaces.

*Pattern.*—The adaxial leaf surfaces are predominately silver green with two shades of darker green speckles along the leaf margin. Dark green irregular markings radiate out from the midrib along the length of the leaf but are most abundant from approximately the middle of the leaf to the leaf tip. Faint silver green irregular markings extend from the midrib to the leaf margin along the entire length of the leaf.

*Color.*—The predominate color of the adaxial surface of the new leaf is 191 A–B with speckles of 137 A and 138 B along the leaf margin. Irregular markings of 137 A radiate out from the midrib along the length of the leaf, but are most abundant from approximately the middle of the leaf extending to the leaf tip. Faint irregular markings of 191 A extend from the midrib to the leaf margin along the entire length of the leaf. The predominate color of the adaxial surface of the mature leaf is more silver-green than, but closest to, 191 D with speckles of 139 A and 138 A along the leaf margin. Irregular markings greater than, but closest to, 139 A radiate out from the midrib along the length of the leaf but are most abundant from approximately the middle of the leaf extending to the leaf tip. Faint irregular markings of 191 A extend from the midrib to the margin along the entire length of the leaf. The abaxial surface of the new leaf is 146 B. The abaxial surface of the mature leaf is 137 C.

*Axially breaks.*—There are approximately 16 to 20 axially breaks with at least one leaf expanded. Leaves show true color and pattern by the first leaf.

*Inflorescence.*—Typical of Aglaonema and does not have commercial significance.

Roots: Thick white roots with fine laterals.

General observation: Aglanomea 'Silver Frost' has predominately silver-green leaves prominently marked in the center and along the leaf margin with dark green. The plant habit is larger and more spreading than the closest commercial comparison, Aglaonema 'Silver Queen'. Plants of Silver Frost grow rapidly, and have noticeable tolerance to cold. These combined characteristics make Silver Frost a unique new cultivar.

I claim:

1. A new and distinct cultivar of Aglaonema plant named Silver Frost, as illustrated and described.

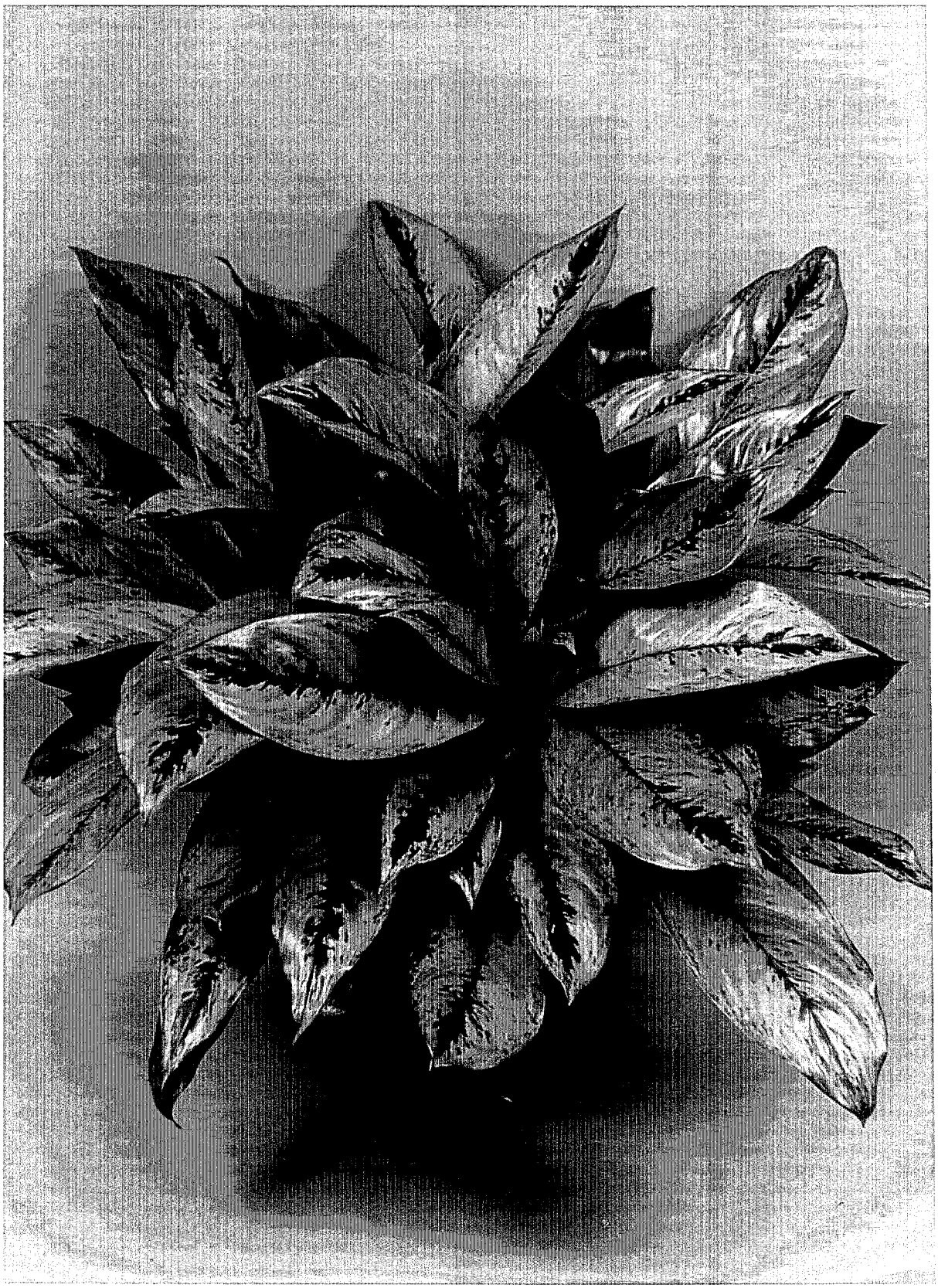

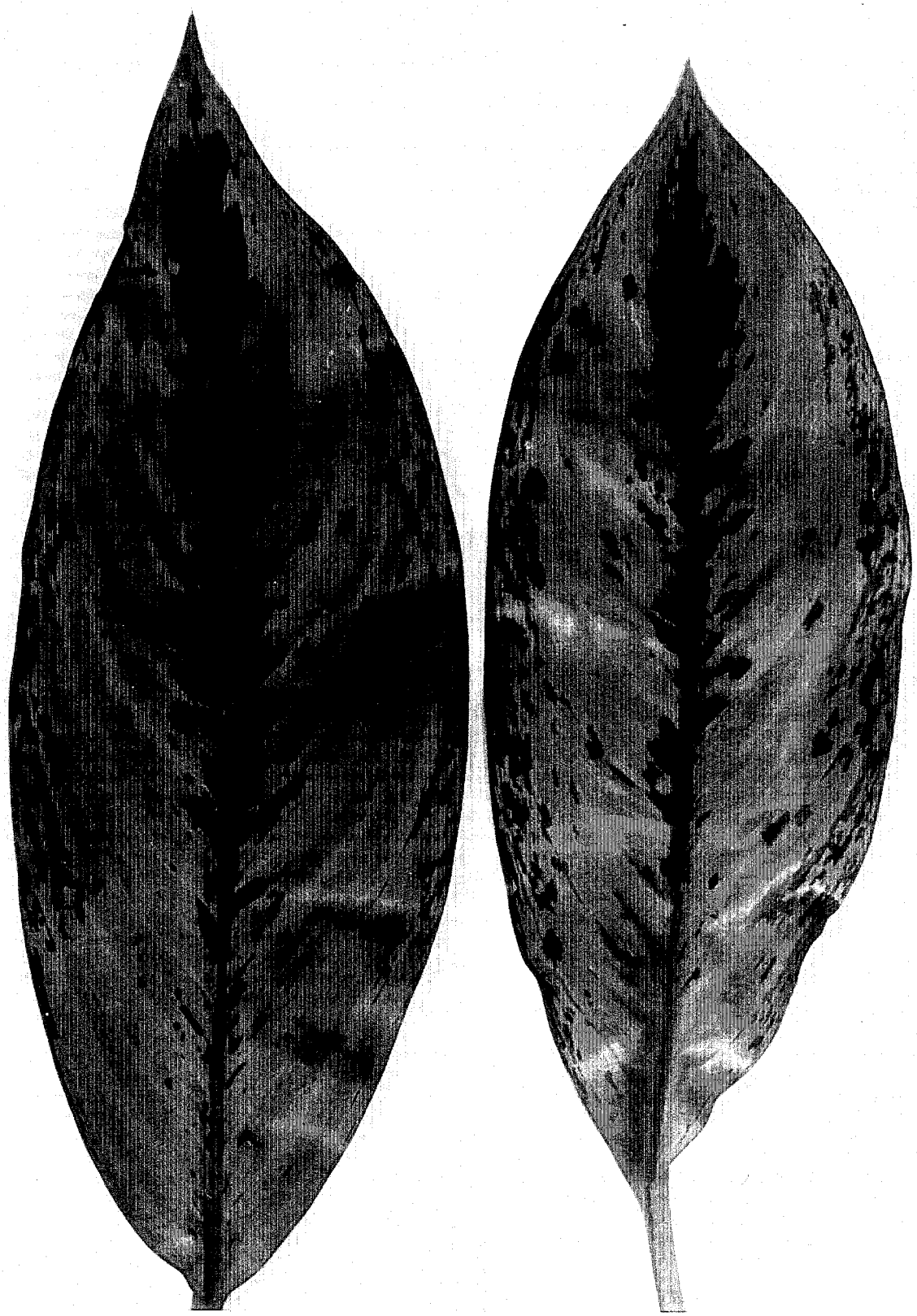

* * * * *